(12) United States Patent
Mizuno et al.

(10) Patent No.: US 8,596,309 B2
(45) Date of Patent: Dec. 3, 2013

(54) MEDICATION MIXING DEVICE AND MEDICATION MIXING METHOD

(75) Inventors: Osamu Mizuno, Osaka (JP); Akinobu Okuda, Nara (JP); Tohru Nakamura, Osaka (JP)

(73) Assignee: Panasonic Corporation, Osaka (JP)

( * ) Notice: Subject to any disclaimer, the term of this patent is extended or adjusted under 35 U.S.C. 154(b) by 472 days.

(21) Appl. No.: 13/000,053

(22) PCT Filed: Mar. 17, 2010

(86) PCT No.: PCT/JP2010/001893
§ 371 (c)(1),
(2), (4) Date: Dec. 20, 2010

(87) PCT Pub. No.: WO2010/113401
PCT Pub. Date: Oct. 7, 2010

(65) Prior Publication Data
US 2011/0100501 A1    May 5, 2011

(30) Foreign Application Priority Data
Mar. 31, 2009   (JP) .................................. 2009-084546

(51) Int. Cl.
*B65B 3/04*    (2006.01)

(52) U.S. Cl.
USPC .................................. 141/27; 141/2; 141/104

(58) Field of Classification Search
USPC ....................... 141/2, 18, 21, 25, 27, 100, 104
See application file for complete search history.

(56) References Cited

U.S. PATENT DOCUMENTS 3,807,467 A * 4/1974 Tascher et al. ................. 141/375
5,037,390 A * 8/1991 Raines et al. .................... 604/83
(Continued)

FOREIGN PATENT DOCUMENTS

| CN | 1657946 | 8/2005 |
| CN | 1980833 | 6/2007 |

(Continued)

OTHER PUBLICATIONS

International Search Report issued Jun. 22, 2010 in International (PCT) Application No. PCT/JP2010/001893.

(Continued)

*Primary Examiner* — Gregory Huson
*Assistant Examiner* — Nicolas A Arnett
(74) *Attorney, Agent, or Firm* — Wenderoth, Lind & Ponack, L.L.P.

(57) ABSTRACT

A medicine mixing device includes a pedestal, a main rotating-base, a sub rotating-base, and a control unit. The pedestal is used to place medicine containers thereon. The main rotating-base includes a holding portion and a main rotating shaft, and rotates around the main rotating shaft. The holding portion holds a syringe for sucking a medicine at its center on its vertical plane. The main rotating shaft is orthogonal to the vertical plane. The sub rotating-base is disposed close to a part of the circumference of the main-rotating base and rotates relatively with respect to the main rotating-base. The sub rotating-base includes a fixing unit and a sub rotating shaft parallel to the main rotating shaft. The fixing unit fixes thereto one medicine container selected from the medicine containers on the pedestal. The control unit controls a medicine to be sucked out of the medicine container into the syringe.

10 Claims, 14 Drawing Sheets

(56) References Cited

U.S. PATENT DOCUMENTS

| | | | |
|---|---|---|---|
| 5,329,976 A * | 7/1994 | Haber et al. | 141/25 |
| 5,911,252 A * | 6/1999 | Cassel | 141/234 |
| 7,017,623 B2 * | 3/2006 | Tribble et al. | 141/27 |
| 7,163,031 B2 | 1/2007 | Graves et al. | |
| 7,537,736 B2 | 5/2009 | Itoh | |
| 7,753,085 B2 * | 7/2010 | Tribble et al. | 141/2 |
| 7,783,383 B2 * | 8/2010 | Eliuk et al. | 700/245 |
| 7,900,658 B2 * | 3/2011 | Osborne et al. | 141/2 |
| 7,913,720 B2 * | 3/2011 | Tribble et al. | 141/27 |
| 8,225,824 B2 * | 7/2012 | Eliuk et al. | 141/192 |
| 8,267,129 B2 * | 9/2012 | Doherty et al. | 141/330 |
| 8,286,671 B1 * | 10/2012 | Strangis | 141/9 |
| 8,316,898 B2 * | 11/2012 | Zinger et al. | 141/27 |
| 8,408,257 B2 * | 4/2013 | Ono et al. | 141/284 |
| 2004/0154690 A1 * | 8/2004 | Osborne et al. | 141/27 |
| 2005/0186119 A1 | 8/2005 | Itoh | |
| 2005/0252574 A1 | 11/2005 | Khan et al. | |
| 2006/0049209 A1 * | 3/2006 | Baker | 222/252 |
| 2008/0114328 A1 * | 5/2008 | Doherty et al. | 604/414 |
| 2012/0241043 A1 * | 9/2012 | Perazzo et al. | 141/2 |

FOREIGN PATENT DOCUMENTS

| | | | | |
|---|---|---|---|---|
| JP | 1-244759 | | 9/1989 | |
| JP | 2003-302411 | | 10/2003 | |
| JP | 2005-233765 | | 9/2005 | |
| JP | 2006-340999 | | 12/2006 | |
| JP | 2008-132232 | | 6/2008 | |
| JP | 2012223372 | * | 11/2012 | A61J 3/00 |
| WO | 2006/132023 | | 12/2006 | |

OTHER PUBLICATIONS

Partial English translation of JP 01-244759, Sep. 1989.

Full machine English translation of JP 2008-132232, Jun. 2008.

\* cited by examiner

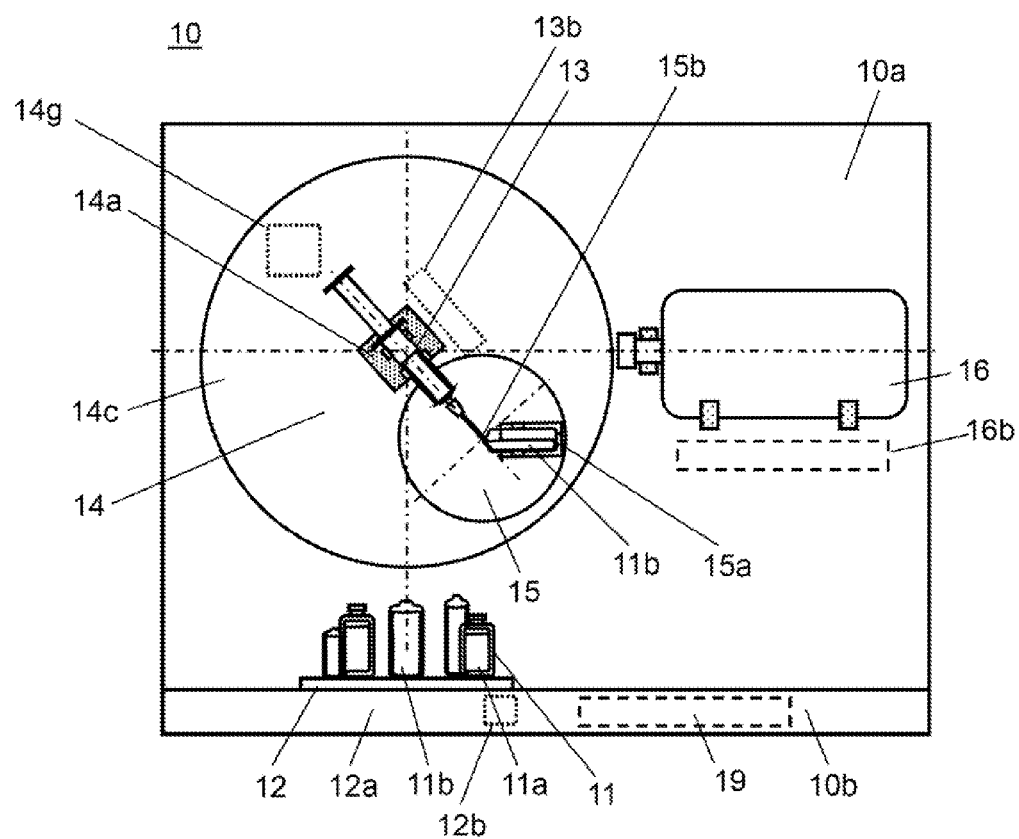

MEDICATION MIXING DEVICE AND MEDICATION MIXING METHOD

TECHNICAL FIELD

The invention relates to a device and method for mixing medicines such as injection medicines by sucking them into a syringe in hospitals and other facilities.

BACKGROUND ART

It is often the case in hospitals and other facilities that different medicines taken out of different types of medicine containers are mixed and given to in- and out-patients. The operation of mixing medicines is usually done manually by nurses and pharmacists, for whom it is a heavy burden. Moreover, the operation of mixing medicines is complicated and difficult when the medicine containers have variety in type and shape, requiring the medicines in these containers to be sucked into a syringe differently from each other.

To reduce these inconveniences, there has been suggested a device for sucking medicines from medicine containers reliably and safely without human operation (see, for example, Patent Literature 1).

FIG. 16 is a configuration of a radioactive medicine dispensing device of Patent Literature 1.

Radioactive medicine dispensing device 30 shown in FIG. 16 is a device for dispensing radioisotope, which is a radioactive medicine as hard or harder to be handled than medicines used in hospitals and other facilities. In device 30, a radioactive medicine is dispensed from storage container 31 located at the top of device 30 into mixing container 34 located at the bottom of device 30 through injection syringe 35 by means of lift mechanism 32 and rotation mechanism 33. Since radioactive medicines should be handled with great care, storage container 31 is fixed to container holder 36 located at the top of device 30. Injection syringe 35 sucks the radioactive medicine by sticking its needle 35a into storage container 31, and moves to mixing container 34. Then, a necessary amount of the radioactive medicine is taken out of injection syringe 35 into mixing container 34.

This structure allows radioactive medicines to be handled reliably and safely without human operation.

The above-described conventional technique, however, handles specific radioactive medicines which are required to be securely fixed for safety. Thus, the technique can handle only one radioactive medicine in one operation, and cannot be used to mix a plurality of medicines contained in a plurality of medicine containers.

CITATION LIST

Patent Literature 1: Japanese Patent Unexamined Publication No. H01-244759

SUMMARY OF THE INVENTION

In order to solve the aforementioned problem, the invention provides a device for efficiently mixing a plurality of medicines contained in a plurality of types of medicine containers, and a method for appropriately mixing these medicines.

The medicine mixing device of the invention includes a pedestal on which medicine containers are placed; a main rotating base including a holding portion and a main rotating shaft, and rotating around the main rotating shaft, the holding portion holding a syringe for sucking a medicine at the center thereof on the vertical plane thereof, and the main rotating shaft being orthogonal to the vertical plane; a sub rotating base placed on the main rotating base and rotating relatively with respect to the main rotating base, the sub rotating base including a fixing unit and a sub rotating shaft parallel to the main rotating shaft, the fixing unit fixing thereto one medicine container selected from the medicine containers on the pedestal; and a control unit for controlling a medicine to be sucked out of the fixed medicine container into the syringe.

The device with this structure can, by itself, handle medicines and medicine containers with different handling characteristics by placing the medicine containers in the respective postures that are the most suitable for them to be handled, thereby mixing a plurality of medicines quickly and efficiently.

The method for mixing medicines of the invention includes: verifying medicines in medicine containers placed on a pedestal by a detection unit; selecting one of the medicine containers based on data for medicines to be mixed; fixing the selected medicine container to a fixing unit of a sub rotating base; holding the fixed medicine container by the sub rotating base; and sucking a medicine out of the medicine container into a syringe held in a holding portion at a center of a main rotating base.

With this method, medicines and medicine containers with different handling characteristics can be handled by a single device by placing the medicine containers in the respective postures that are the most suitable for them to be handled, allowing a plurality of medicines to be mixed quickly and efficiently.

BRIEF DESCRIPTION OF THE DRAWINGS

FIG. 14 is a front view in which, when the medicine container is an ampule, the medicine contained in the ampule is sucked into a syringe by placing the ampule at a predetermined angle and a predetermined height.

DESCRIPTION OF EMBODIMENTS

Figure 1A:
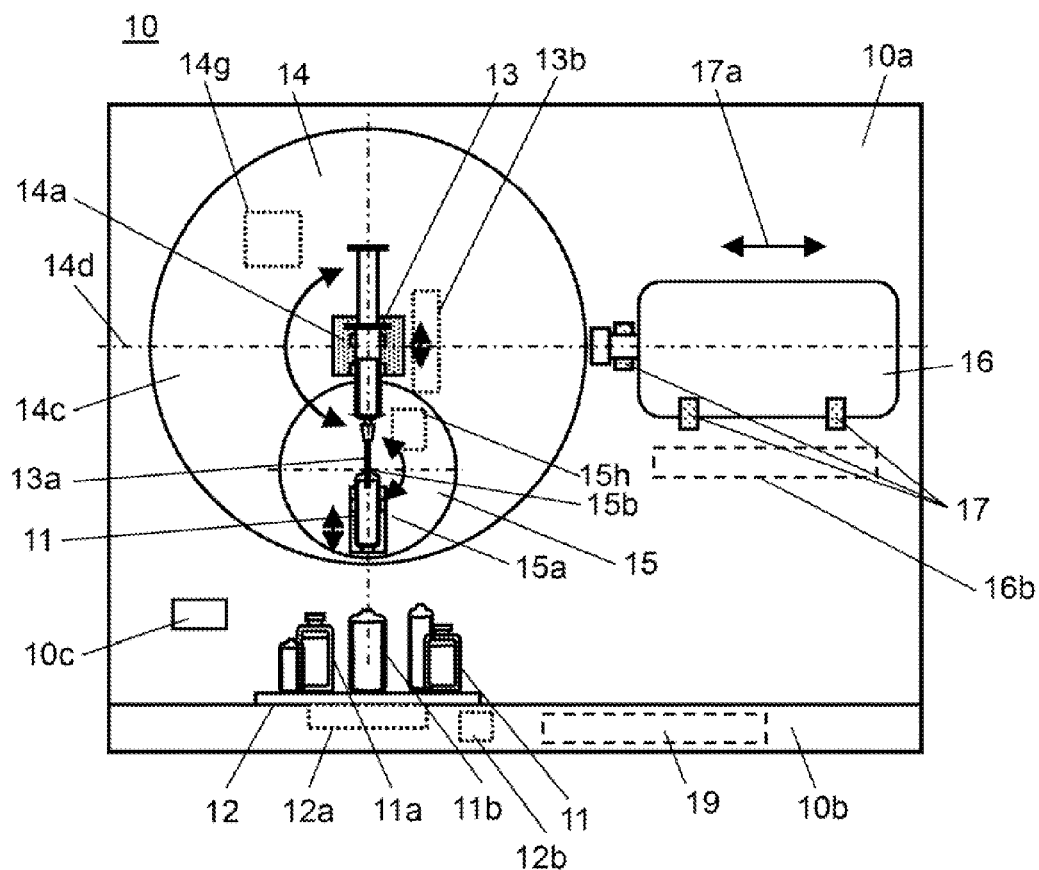
FIG. 1A is a schematic front view of a medicine mixing device according to a first embodiment of the invention.

Embodiments of the invention will be described as follows with reference to the drawings. In the second embodiment, like components are labeled with like reference numerals with respect to the first embodiment, and the description thereof is partially omitted. The drawings are schematically shown for easier understanding with only main components thereof.

First Embodiment

Figure 1B:
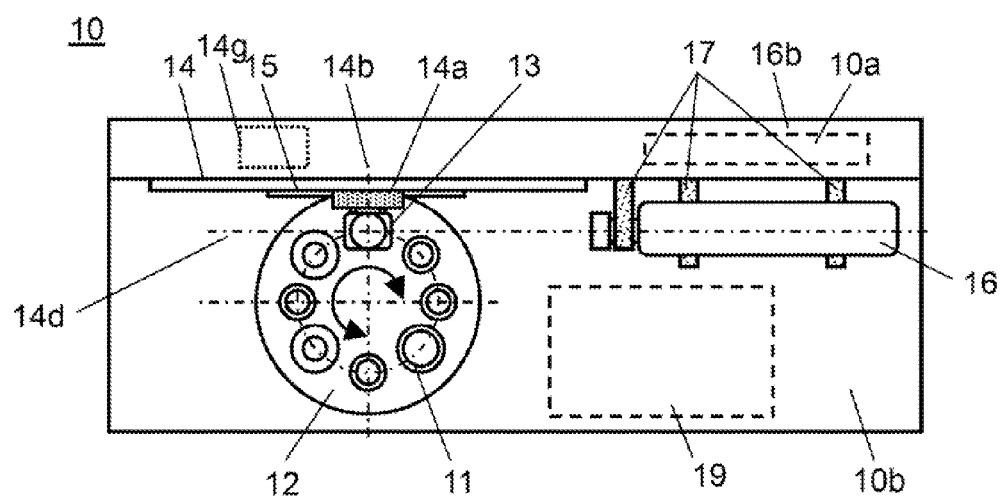
FIG. 1B is a schematic plan view of the medicine mixing device according to the first embodiment of the invention.
Figure 2:
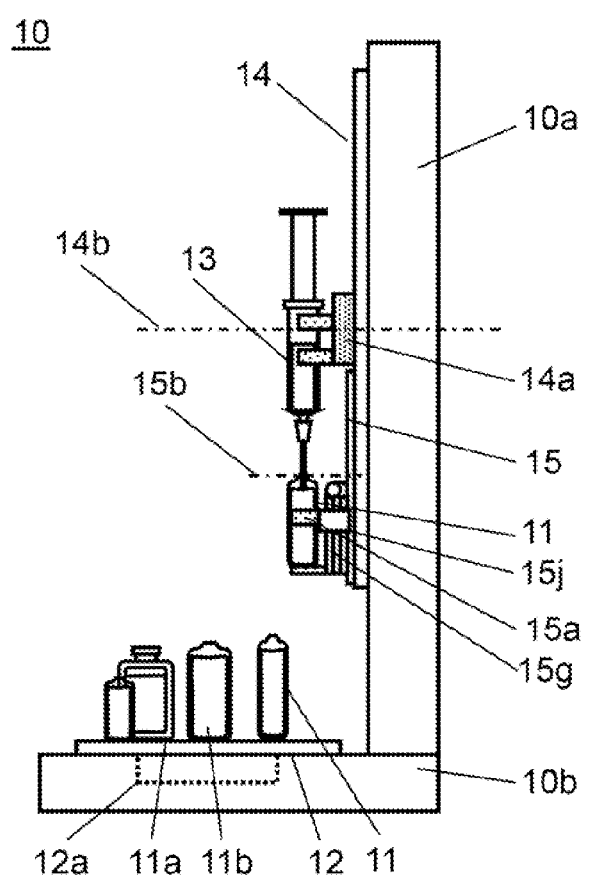
FIG. 2 is a schematic side view of the medicine mixing device according to the first embodiment of the invention.

FIGS. 1A and 1B are a schematic front view and a schematic plan view, respectively, of medicine mixing device 10 according to the first embodiment of the invention. FIG. 2 is a schematic side view of device 10 in which infusion bag 16 is not shown.

As shown in FIGS. 1A, 1B, and 2, medicine mixing device 10 includes
pedestal 12 on which medicine containers 11 are placed, syringe 13 for sucking a medicine, main rotating base 14, sub rotating base 15, and control unit 19. Main rotating base 14 includes holding portion 14a and main rotating shaft 14b, and rotates around main rotating shaft 14b. Holding portion 14a holds syringe 13 at its center on its vertical plane, and main rotating shaft 14b is orthogonal to the vertical plane. Sub rotating base 15 includes fixing unit 15a and sub rotating shaft 15b parallel to main rotating shaft 14b. Fixing unit 15a fixes thereto medicine container 11 selected from those on pedestal 12. Sub rotating base 15 is disposed to be close to a part of circumference 14c of main rotating base 14, and rotates around sub rotating shaft 15b relatively with respect to main rotating base 14.

The device with this structure can, by itself, handle medicine containers with different handling characteristics by placing them in the respective postures that are the most suitable for them to be handled as described in detail later, thereby mixing a plurality of medicines quickly and efficiently.

In medicine mixing device 10 of the present first embodiment, medicine containers 11 include vial 11a (a first medicine container) and ampule 11b (a second medicine container).

In the case of sucking a medicine out of vial 11a selected from medicine containers 11, control unit 19 operates main and sub rotating bases 14 and 15 in liaison with each other such that vial 11a is placed upside down right above syringe 13 and that the medicine in vial 11a is sucked into syringe 13.

In the case of sucking a medicine out of ampule 11b selected from medicine containers 11, on the other hand, control unit 19 places ampule 11b upright right under syringe 13 first. Then, as the amount of the medicine in ampule 11b decreases, control unit 19 operates main and sub rotating bases 14 and 15 in liaison with each other such that ampule 11b is moved upward in the vertical direction and that the medicine in ampule 11b is sucked into syringe 13.

When medicines and medicine containers 11 such as vial 11a and ampule 11b have different handling characteristics, medicine containers 11 can be placed in the respective postures that are the most suitable for them to be handled. Thus, the device can, by itself, handle a plurality of types of medicine containers, thereby mixing a plurality of types of medicines quickly and without waste. The above-described operations will each be described in detail later.

In this device, the first medicine container may be ampule 11b instead of vial 11a, and the second medicine container may be a vial 11a instead of ampule 11b.

In this case, too, a plurality of types of medicines can be mixed quickly and without waste.

As shown in FIGS. 1A and 1B, medicine mixing device 10 further includes infusion holder 17 for holding infusion bag 16. Infusion holder 17 includes transfer mechanism 16b, which allows infusion bag 16 to get closer or further away from syringe 13 in the direction of arrow 17a. Transfer mechanism 16b, which is attached to sidewall 10a of device 10, includes a drive unit for horizontally moving infusion bag 16 held by infusion holder 17.

When a medicine is sucked into syringe 13 beyond a predetermined amount, it can be injected into infusion bag 16 by approaching infusion bag 16 to syringe 13.

In medicine mixing device 10, main rotating base 14 is rotatably placed on sidewall 10a, and sub rotating base 15 is rotatably placed on main rotating base 14. Pedestal 12 having medicine containers 11 thereon is placed rotatably and slidably on base 10b. Main rotating base 14 is driven by drive unit 14g provided in sidewall 10a, and sub rotating base 15 is driven by drive unit 15h provided therein. Sub rotating base 15 holds slide rail 15g which is folded and held by holding portion 15j as described later when medicine container 11 is held.

Pedestal 12 shown in FIGS. 1A, 1B, and 2 is a turntable which is detachable from base 10b and portable. Therefore, medicine containers 11 can be placed in other locations than medicine mixing device 10, such as a medicine shelf (not shown) from which they are taken out by nurses and pharmacists, or a medicine storage room (not shown) for medicines under closely supervised conditions. This increases the convenience of collecting necessary medicine containers 11.

Pedestal 12 further includes revolver 12a having a motor (not shown) at its bottom, and is rotatably driven by revolver 12a.

Revolver 12a allows nurses and pharmacists to select necessary medicine containers 11 from those placed on pedestal 12 quickly, thereby improving the selective operability.

As shown in FIG. 1A, sidewall 10a includes sensor unit 10c, which distinguishes the shape and type of medicine containers 11 on pedestal 12. Sensor unit 10c includes a light-emitting device and a light-receiving device, thereby generating light and then scanning, for example, the bar codes on medicine containers 11.

When a medicine in medicine container 11 contains both liquid and powdery components, these components must be mixed before being sucked into syringe 13. For times like this, in addition to the function of rotating pedestal 12, the function of rotating each medicine container 11 on its axis is provided by means of drive unit 12b. The rotation of pedestal 12 and the rotation of each medicine container 11 allow the powdery component of a medicine in medicine container 11 to be dissolved in the liquid component of the medicine.

The following is a description of a method for mixing a plurality of medicines by using medicine mixing device 10 described above. Representative examples of medicine containers 11 containing a plurality of medicines to be mixed include vials and ampules.

FIGS. 3A to 3F show principal processes of sucking medicine 11c out of vial 11a into syringe 13 through needle 13a. FIGS. 4A to 4D show principal processes of sucking medicine 11c out of ampule 11b into syringe 13 through needle 13a.

Figure 3A:
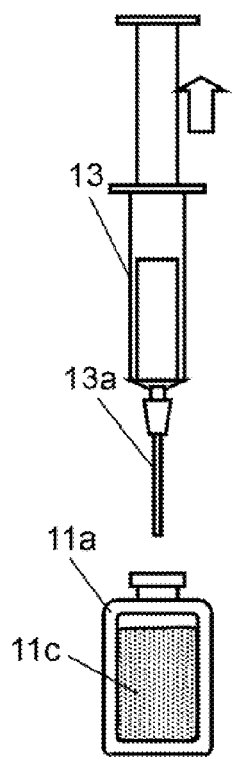
FIG. 3A shows a process of sucking a medicine in a first medicine container into a syringe through a needle.
Figure 3B:
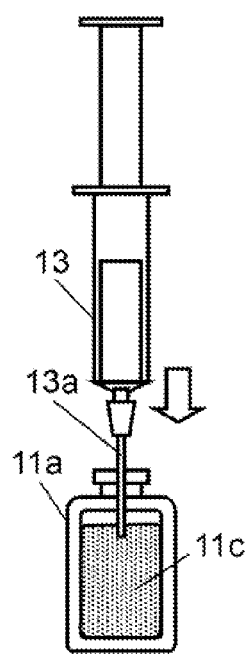
FIG. 3B shows another process of sucking the medicine in the first medicine container into the syringe through the needle.
Figure 3C:
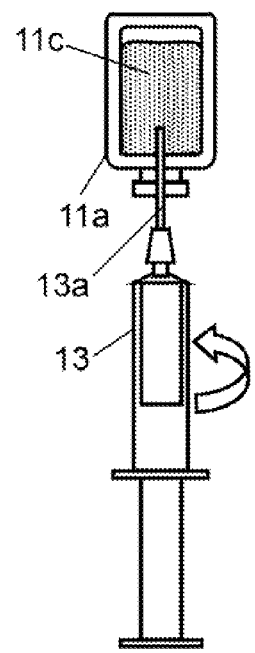
FIG. 3C shows another process of sucking the medicine in the first medicine container into the syringe through the needle.
Figure 3D:
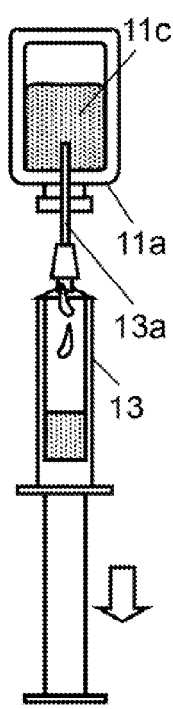
FIG. 3D shows another process of sucking the medicine in the first medicine container into the syringe through the needle.
Figure 3E:
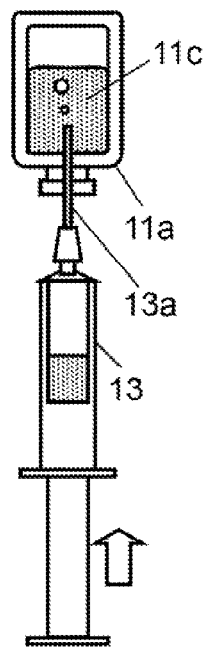
FIG. 3E shows another process of sucking the medicine in the first medicine container into the syringe through the needle.
Figure 3F:
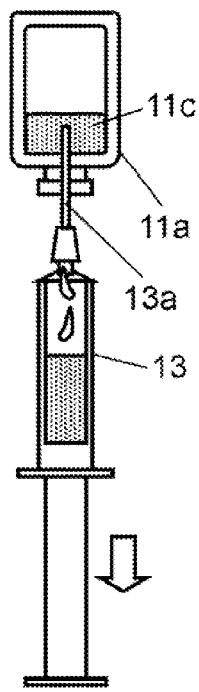
FIG. 3F shows another process of sucking the medicine in the first medicine container into the syringe through the needle.

In FIG. 3A, before sucking medicine 11c out of vial 11a, air is sucked into syringe 13. In FIG. 3B, needle 13a of syringe 13 is inserted into vial 11a. In FIG. 3C, vial 11a and syringe 13 with needle 13a are turned 180 degrees vertically. In FIG. 3D, medicine 11c is sucked into syringe 13. In FIG. 3E, when a predetermined amount of medicine 11c is sucked, the air in syringe 13 is discharged into vial 11a. In FIG. 3F, after an appropriate amount of air is discharged, the medicine is sucked out of vial 11a into syringe 13 again. These series of operations are repeated to suck medicine 11c out of vial 11a into syringe 13.

Figure 4A:
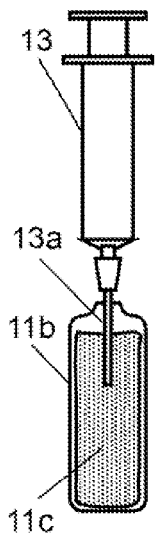
FIG. 4A shows a process of sucking a medicine in a second medicine container into a syringe through a needle.
Figure 4B:
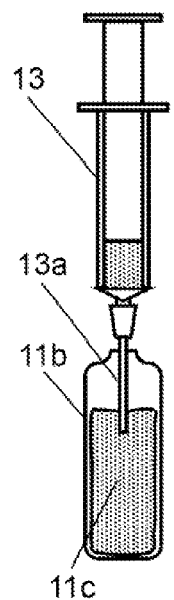
FIG. 4B shows another process of sucking the medicine in the second medicine container into the syringe through the needle.
Figure 4C:
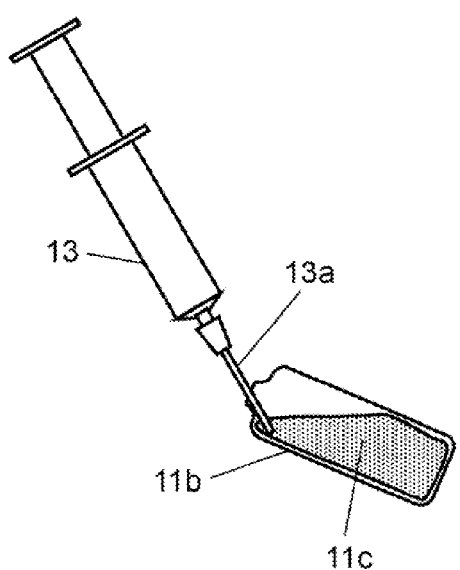
FIG. 4C shows another process of sucking the medicine in the second medicine container into the syringe through the needle.
Figure 4D:
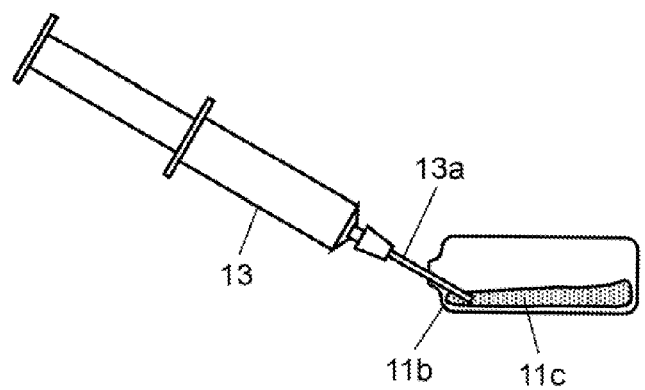
FIG. 4D shows another process of sucking the medicine in the second medicine container into the syringe through the needle.

Medicine 11c is sucked out of ampule 11b, on the other hand, as follows. In FIG. 4A, needle 13a of syringe 13 is inserted into the mouth of ampule 11b, and medicine 11c is sucked out of ampule 11b standing upright. In FIG. 4C, before it gets too far for the tip of needle 13a to reach the surface (liquid level) of medicine 11c in ampule 11b standing upright, ampule 11b is inclined to continue the sucking. In FIG. 4D, when the amount of medicine 11c is further decreased, ampule 11b is laid down so that almost all of medicine 11c in ampule 11b can be sucked into syringe 13.

Medicine mixing device 10 of the present first embodiment is structured to suck medicine 11c out of vial 11a (the first medicine container) or ampule 11b (the second medicine container) shown in FIGS. 3A-3F and 4A-4D, respectively, into syringe 13.

A method for mixing medicines by using medicine mixing device 10 will be described in detail as follows.

Figure 5:
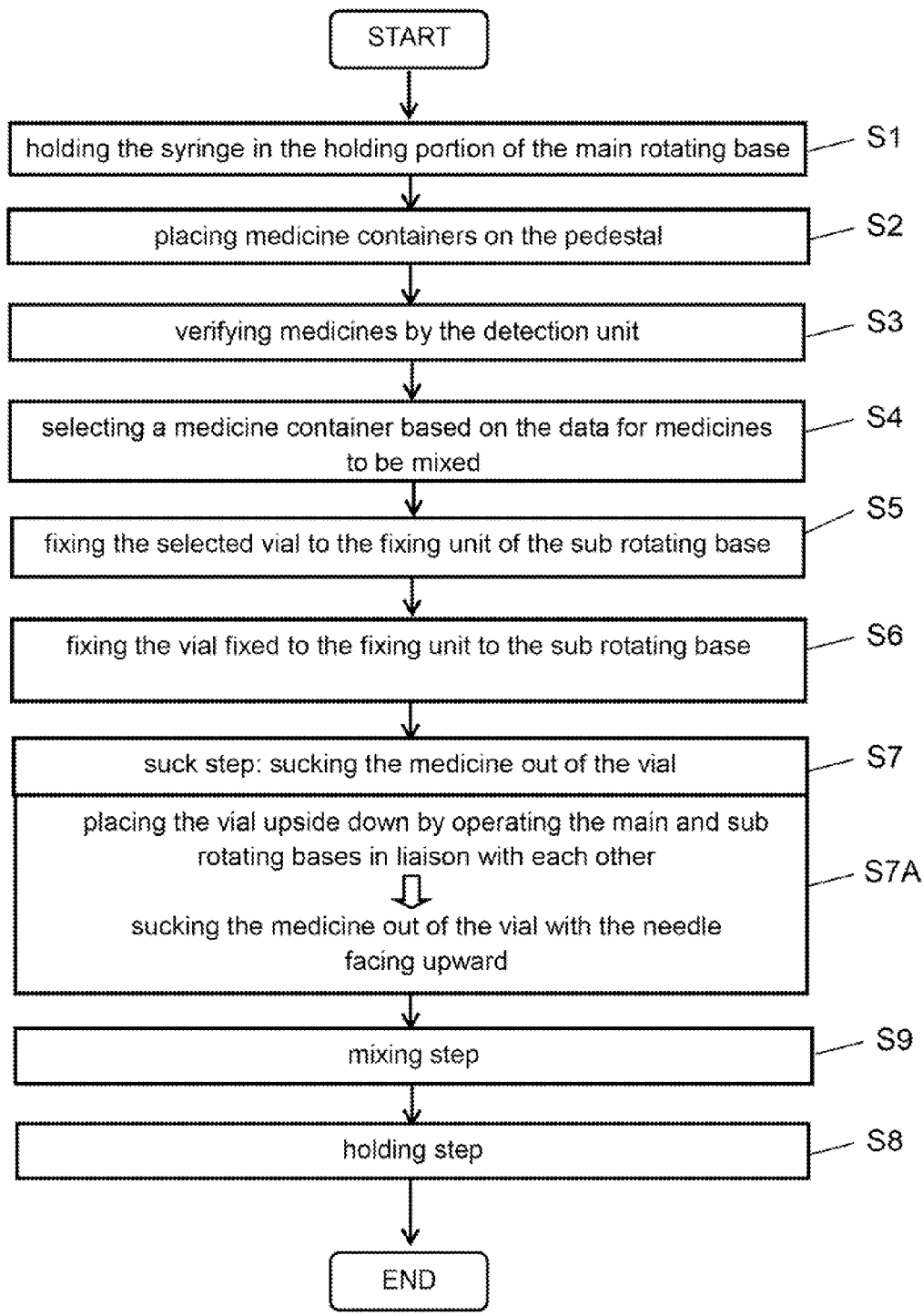
FIG. 5 is a flowchart showing a method for mixing medicines according to the first embodiment of the invention (when the medicine container is a vial).
Figure 6:
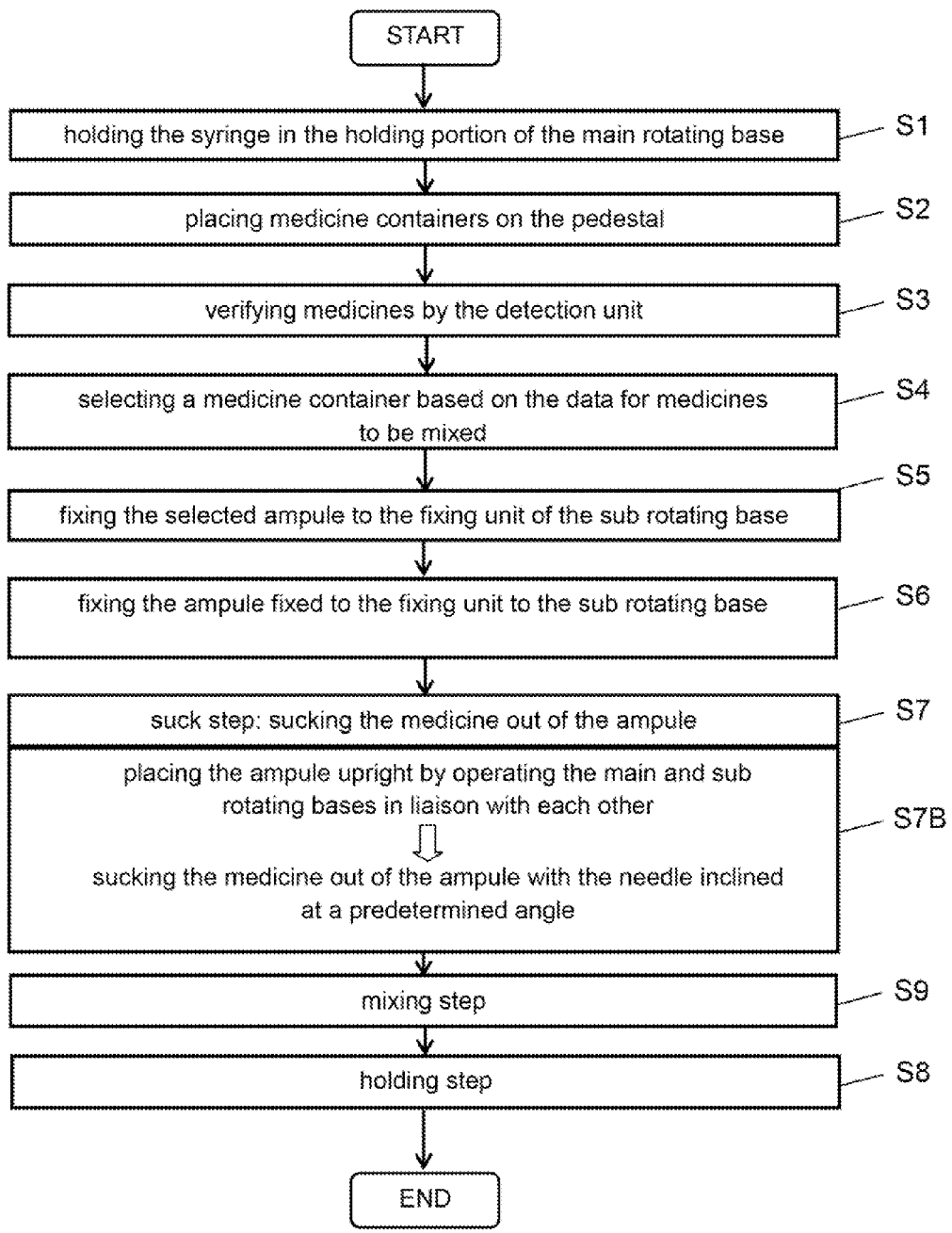
FIG. 6 is a flowchart showing a method for mixing medicines according to the first embodiment of the invention (when the medicine container is an ampule).

FIGS. 5 and 6 show flowcharts showing the method for mixing medicines according to the first embodiment of the invention. FIG. 5 is a flowchart when medicine container 11 is vial 11a, and FIG. 6 is a flowchart when medicine container 11 is ampule 11b.

The method for mixing medicines according to the present first embodiment performs Steps S1 to S9 shown in FIG. 5 by using medicine mixing device 10 of FIGS. 1A and 1B. Step S3 is a step for verifying the type and amount of medicine 11c in medicine container 11 and the presence or absence of particulates in medicine 11c by means of a detection unit. The detection unit can be, for example, sensor unit 10c shown in FIGS. 1A and 1B including at least the light-emitting device and the light-receiving device. Sensor unit 10c emits light to medicine 11c and detects the reflected light, thereby detecting the type and amount of medicine 11c in medicine container 11 and the presence or absence of particulates in medicine 11c. Step S4 is a step for selecting one of medicine containers 11 based on data for medicines to be mixed. This data indicates the type, amount, and mixing conditions of medicines to be mixed based on prescriptions from doctors. Step S5 is a step for fixing the selected one of medicine containers 11 to fixing unit 15a of sub rotating base 15. Step S6 is a step for holding medicine container 11 fixed to fixing unit 15a by sub rotating base 15 using slide rail 15g and holding portion 15j. Step S7 is a step for sucking medicine 11c out of medicine container 11 into syringe 13 held in holding portion 14a at the center of main rotating base 14. Step S9 is a step for returning medicine container 11 from which medicine 11c has been sucked to the original position on pedestal 12, and repeating the processes of Steps S4 to S7A with the other medicine containers 11, thereby mixing a plurality of medicines 11c in syringe 13.

The method for mixing medicines according to the present first embodiment will be described along with the flowchart of FIG. 5. First, as shown in FIGS. 1A and 1B, syringe 13 into which medicines 11c are to be sucked is held in holding portion 14a at the center of main rotating base 14 (Step S1). A plurality of medicine containers 11 including vial 11a are placed on pedestal 12 (Step S2). Medicines 11c in medicine containers 11 are verified by the detection unit (Step S3). Vial 11a is selected based on the data for medicines to be mixed (Step S4). Vial 11a thus selected is fixed to fixing unit 15a of sub rotating base 15 (Step S5). Vial 11a thus fixed to fixing unit 15a is held by sub rotating base 15 (Step S6). Medicine 11c is sucked out of vial 11a into syringe 13 (Step S7). Vial 11a is placed upside down by operating main and sub rotating bases 14 and 15 in liaison with each other. Needle 13a of syringe 13 is faced upward in the vertical direction and inserted into vial 11a, thereby sucking medicine 11c out of vial 11a (Step S7A). Other medicines 11c are sucked out of other vials 11a into syringe 13 in the same manner, thereby mixing the plurality of medicines 11c efficiently and reliably (Step S9).

With this method, medicines 11c and medicine containers 11 including vials with different handling characteristics can be handled by a single device by placing medicine containers 11 in the respective postures that are the most suitable for, them to be handled, allowing a plurality of medicines 11c to be mixed quickly and without waste.

FIG. 6, on the other hand, shows a flowchart when medicine container 11 is ampule 11b. The method for mixing medicines shown in FIG. 6 performs Steps S1 to S9 in the same manner as in FIG. 5.

The method for mixing medicines according to the present first embodiment will be described along with the flowchart of FIG. 6. First, as shown in FIGS. 1A and 1B, syringe 13 into which medicines 11c are to be sucked is held in holding portion 14a at the center of main rotating base 14 in medicine mixing device 10 (Step S1). A plurality of medicine containers 11 including ampule 11b are placed on pedestal 12 (Step S2). Medicines 11c in medicine containers 11 are verified by the detection unit (not shown) (Step S3). Ampule 11b is selected based on the data for medicines to be mixed (Step S4). Ampule 11b thus selected is fixed to fixing unit 15a of sub rotating base 15 (Step S5). Ampule 11b thus fixed to fixing unit 15a is held by sub rotating base 15 (Step S6). Medicine 11c is sucked out of ampule 11b into syringe 13 (Step S7). Syringe 13 sucks a predetermined amount of medicine 11c out of ampule 11b. Next, main and sub rotating bases 14 and 15 are operated in liaison with each other such that ampule 11b is placed at a predetermined height and at a predetermined angle with needle 13a of syringe 13 in ampule 11b, thereby sucking medicine 11c out of ampule 11b into syringe 13 (Step S7B). Other medicines 11c are sucked out of other ampules 11b into syringe 13 in the same manner, thereby mixing the plurality of medicines 11c efficiently and reliably (Step S9).

With this method, medicines 11c and medicine containers 11 including ampule 11b with different handling characteristics can be handled by a single device by placing medicine containers 11 in the respective postures that are the most suitable for them to be handled, allowing a plurality of medicines 11c to be mixed quickly and without waste.

The method for mixing medicines according to the present embodiment may further include Step S8 for holding infusion bag 16 by infusion holder 17 as shown in the flowcharts of FIGS. 5 and 6. With Step S8, medicine 11c sucked into syringe 13 beyond a predetermined amount can be injected into infusion bag 16. This allows medicines 11c to be sucked out of a plurality of medicine containers 11 and to be mixed without interruption.

With Step S8, when medicine 11c is sucked into syringe 13 beyond a predetermined amount, infusion bag 16 can be moved close to syringe 13 so that medicine 11c can be injected from syringe 13 into infusion bag 16. To achieve this, syringe 13 is moved slidably in axial direction 14d using transfer mechanism 16b of infusion bag 16, thereby inserting or pulling out needle 13a into/from infusion bag 16. Transfer mechanism 16b can also move infusion bag 16 slidably in the direction of arrow 17a along axial direction 14d.

In the method for mixing medicines, medicine container 11 is vial 11a in FIG. 5 and is ampule 11b in FIG. 6, respectively. Alternatively, both vial 11a and ampule 11b can be selected as a plurality of medicine containers 11. In this case, medicines can be mixed based on a combination of the method for mixing medicines shown in the flowchart (FIG. 5) having vial 11a and the method for mixing medicines shown in the flowchart (FIG. 6) having ampule 11b.

The following is a detailed description of principal components used in the method for mixing medicines when medicine container 11 is vial 11a and when medicine container 11 is ampule 11b.

Figure 7:
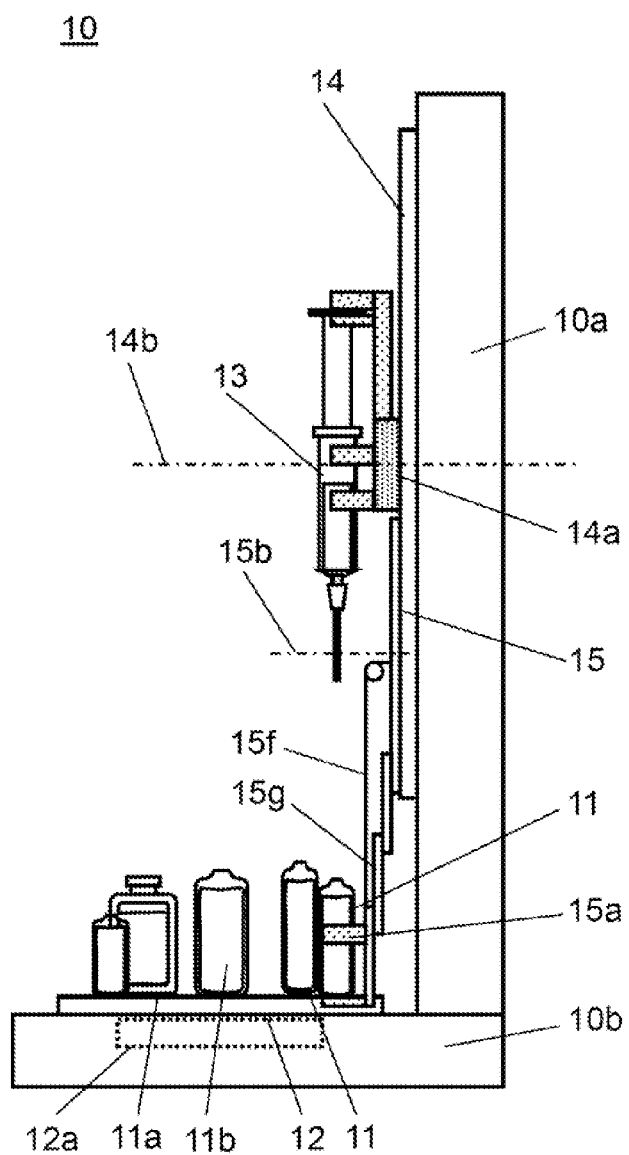
FIG. 7 is a side view in which a medicine container on a pedestal is fixed to the fixing unit of a sub rotating base.

FIG. 7 is a side view in which medicine container 11 on pedestal 12 is fixed to fixing unit 15a of sub rotating base 15. As shown in FIG. 7, the selected medicine container 11 is fixed to fixing unit 15a supported by slide rail 15g extending from sub rotating base 15, and then attached together with fixing unit 15a to the tip of slide rail 15g. Fixing unit 15a to which medicine container 11 has been fixed is pulled at one end thereof vertically upward by wire 15f connected to sub rotating base 15. As a result, slide rail 15g is folded, and medicine container 11 fixed to fixing unit 15a is raised to the position of sub rotating base 15. Then, fixing unit 15a is held at holding portion 15j in sub rotating base 15, thereby fixing medicine container 11 to fixing unit 15a as shown in FIG. 2.

Figure 8:
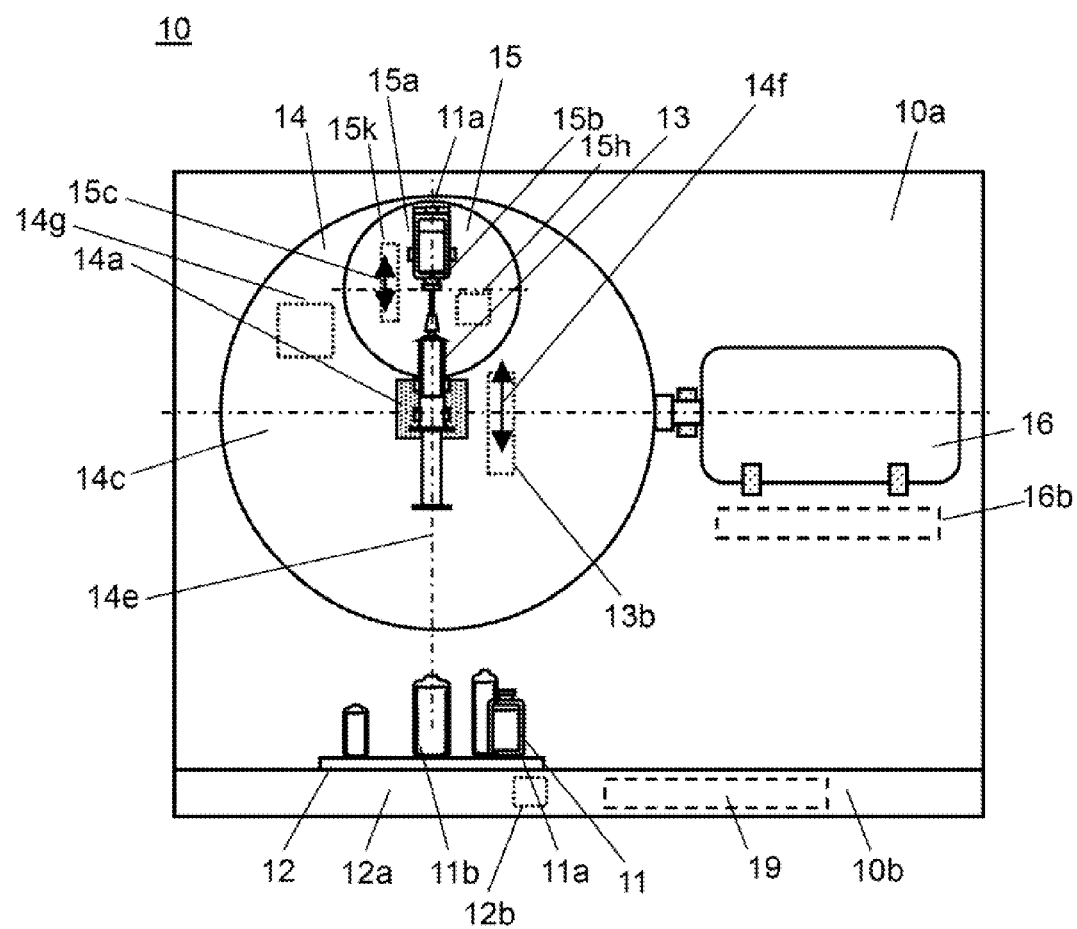
FIG. 8 is a front view in which, when the medicine container is a vial, a medicine is sucked out of the inverted vial.
Figure 9:
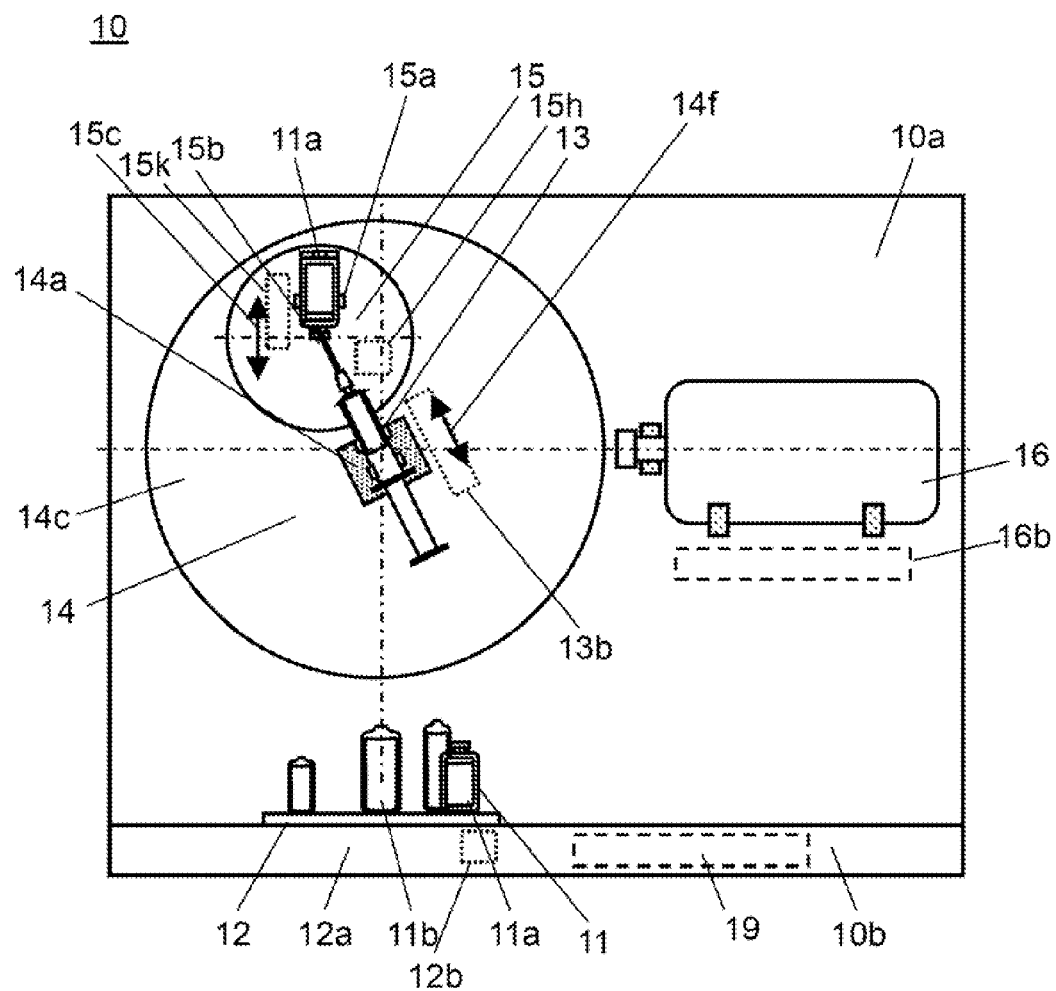
FIG. 9 is a front view in which, when the medicine container is a vial, the syringe is placed inclined at a predetermined angle when the amount of the medicine remaining in the inverted vial is small.

FIG. 8 is a front view in which, when medicine container 11 is vial 11a, medicine 11c is sucked out of the inverted vial 11a. FIG. 9 is a front view in which syringe 13 is placed inclined at a predetermined angle when the amount of medicine 11c remaining in the inverted vial 11a is small. In this case, syringe 13 is inclined as shown in FIG. 9 so that needle 13a can be inserted in an inclined position into vial 11a by operating main and sub rotating bases 14 and 15 in liaison with each other.

The positional relationship between vial 11a and syringe 13 shown in FIG. 8 corresponds to that shown in FIGS. 3C to 3F. As shown in FIG. 8, vial 11a can be positioned upside down, and medicine 11c therein can be efficiently sucked into syringe 13 by adjusting the air pressure in vial 11a while medicine 11c and air are sucked into syringe 13. When the amount of medicine 11c remaining in vial 11a is small, as shown in FIG. 9, needle 13a is inclined with respect to the vertical direction so that medicine 11c can be sucked efficiently by making good use of the obliquely cut surface (not shown) of the tip of needle 13a. With this approach, almost all of medicine 11c can be sucked out.

In FIGS. 8 and 9, holding portion 14a of main rotating base 14 and fixing unit 15a of sub rotating base 15 have respective transfer mechanisms movable in axial directions 14f and 15c, respectively, in their drive units 13b and 15k. These transfer mechanisms and the rotation of main and sub rotating bases 14 and 15 allow adjusting the arrangement relationship (postures) between medicine container 11 and syringe 13. They also allow needle 13a of syringe 13 to be inserted or pulled out into/from medicine container 11 more easily. As a result, medicine 11c can be sucked out efficiently according to its amount in medicine container 11.

FIGS. 10A, 10B, 11A, and 11B are schematic diagrams showing the positional relationship between mouth 11d of medicine container 11 and sub rotating shaft 15b of sub rotating base 15 when needle 13a is inserted in medicine container 11. Medicine container 11 is vial 11a in FIGS. 10A and 10B, and is ampule 11b in FIGS. 11A and 11B; however, in the following description, vial 11a and ampule 11b are uniformly referred to as medicine container 11.

Figure 10A:
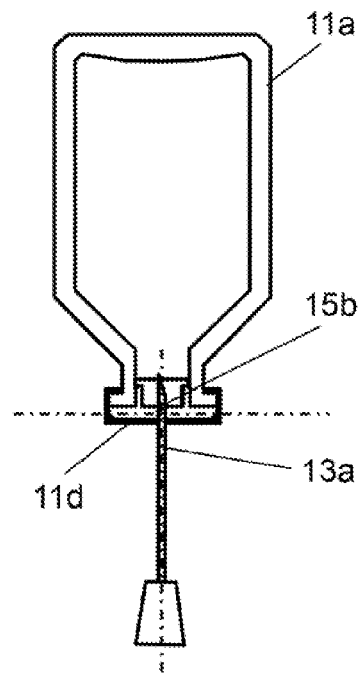
FIG. 10A is a schematic diagram showing the positional relationship between the mouth of the first medicine container and the sub rotating shaft of the sub rotating base when the needle is inserted in the first medicine container.
Figure 10B:
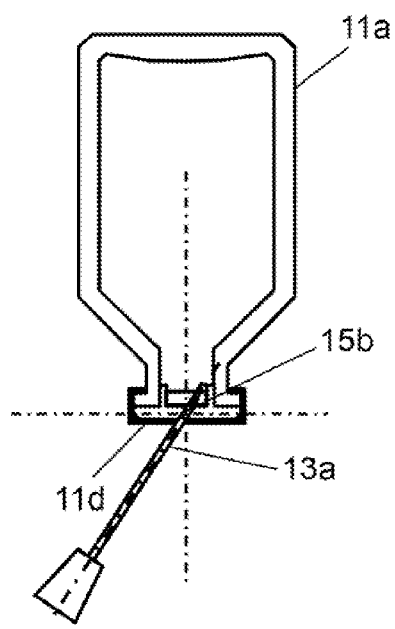
FIG. 10B is another schematic diagram showing the positional relationship between the mouth of the first medicine container and the sub rotating shaft of the sub rotating base when the needle is inserted in the first medicine container.
Figure 11A:
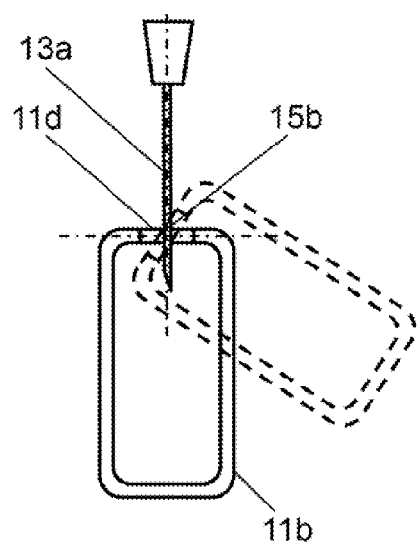
FIG. 11A is a schematic diagram showing the positional relationship between the mouth of the second medicine container and the sub rotating shaft of the sub rotating base when the needle is inserted in the second medicine container.

As shown in FIGS. 10A and 11A, the position of mouth lid of medicine container 11 held on sub rotating base 15 is adjusted to coincide with sub rotating shaft 15b, which is at the center of sub rotating base 15. This allows the part of needle 13a that is a little below its tip to be adjusted to coincide with sub rotating shaft 15b as shown in FIG. 10B, thereby increasing the range of angles at which needle 13a can be inserted into medicine container 11. As a result, almost all of medicine 11c in medicine container 11 can be sucked out.

In FIG. 11A, when medicine container 11 is turned around sub rotating shaft 15b shown by dotted lines, the position of mouth 11d and the part of needle 13a that is a little below its tip are made to coincide with sub rotating shaft 15b in the same manner as in FIGS. 10A and 10B. This also increases the range of angles at which needle 13a can be inserted into medicine container 11, allowing almost all of medicine 11c in medicine container 11 to be sucked out.

Figure 11B:
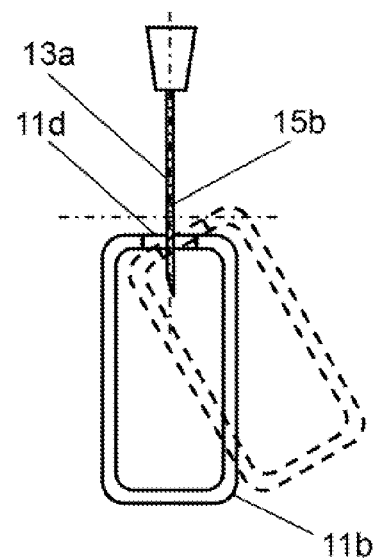
FIG. 11B is another schematic diagram showing the positional relationship between the mouth of the second medicine container and the sub rotating shaft of the sub rotating base when the needle is inserted in the second medicine container.

In FIG. 11B, on the other hand, when the position of mouth 11d and the part of needle 13a that is a little below its tip are displaced from sub rotating shaft 15b, this decreases the range of angles at which needle 13a can be inserted into medicine container 11. As a result, it becomes difficult to suck medicine 11c out efficiently.

Figure 12:
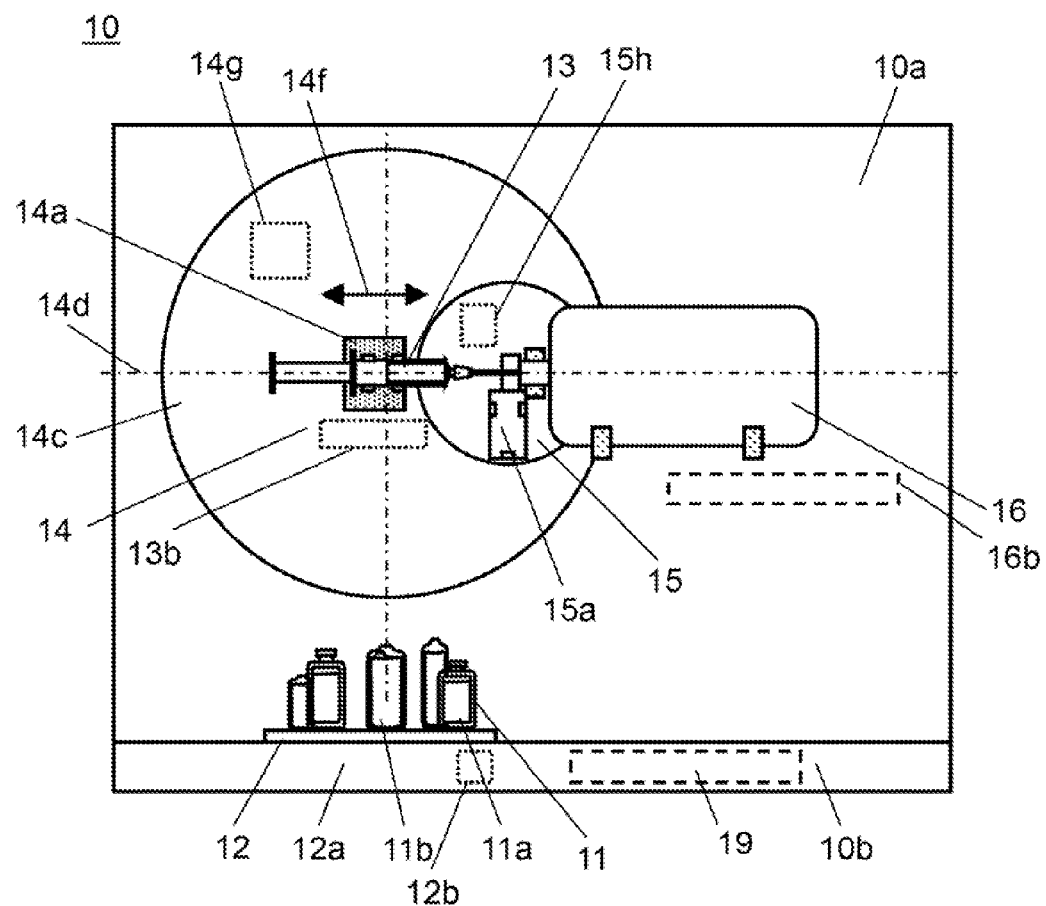
FIG. 12 is a front view in which the needle of the syringe is inserted into an infusion bag so as to inject the medicine thereinto.

FIG. 12 is a front view in which needle 13a of syringe 13 is inserted into infusion bag 16 so that medicine 11c is injected thereinto when sucked into syringe 13 beyond a predetermined amount. As a result, syringe 13 becomes empty, allowing the medicine in another medicine container 11 to be sucked into syringe 13.

In this case, both infusion bag 16 and syringe 13 can be moved in axial direction 14d until being disposed in a desired positional relationship so as to inject medicine 11c.

Figure 13:
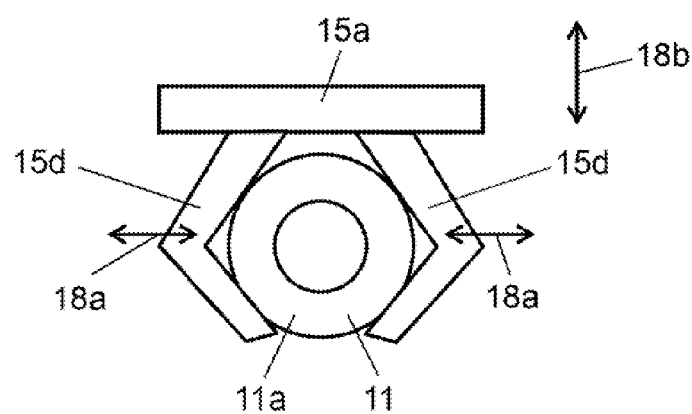
FIG. 13 is a plan view in which the medicine container is held by the sub rotating base.

FIG. 13 is a plan view in which medicine container 11 is held by sub rotating base 15. In FIG. 13, vial 11a as medicine container 11 is held between a pair of arms 15d of sub rotating base 15 (not shown).

In FIG. 13, fixing unit 15a of sub rotating base 15 includes a retention mechanism for holding medicine container 11 such that its center coincides with needle 13a (not shown) of syringe 13 (not shown). This retention mechanism may include arms 15d. Medicine containers 11 with different shapes have different mouth diameters. In this case, the mouth diameters are determined by previously measuring the shapes of medicine containers 11 or by providing a camera or other image capture devices for monitoring medicine container 11 above medicine mixing device 10. The camera or other image capture devices may be disposed as a detection unit in sensor unit 10c.

After medicine container 11 is securely held by moving the pair of arms 15d in the direction of arrow 18a according to the mouth diameter of medicine container 11, the entire fixing unit 15a is moved in the direction of arrow 18b for positioning. As a result, the center of medicine container 11 is centered to coincide with needle 13a (not shown) of syringe 13 (not shown).

The accurate centering of the center of medicine container 11 allows the sucking operation to be performed without applying too much stress to syringe 13 or needle 13a even when medicine container 11 changes its posture due to the rotation of main and sub rotating bases 14 and 15.

FIG. 14 is a front view in which, when medicine container 11 is ampule 11b, medicine 11c contained in ampule 11b is sucked into syringe 13 by placing ampule 11b at a predetermined angle.

In FIG. 14, the positional relationship between syringe 13 and ampule 11b shown in FIG. 4D is shown in medicine mixing device 10 of the present first embodiment. In FIG. 14, ampule 11b is placed at a predetermined height and at a predetermined angle with needle 13a of syringe 13 inserted in ampule 11b by operating main and sub rotating bases 14 and 15 in liaison with each other. With syringe 13 and ampule 11b thus disposed, medicine 11c in ampule 11b is sucked into syringe 13.

Since syringe 13 with needle 13a and ampule 11b are thus positioned at a predetermined height and at a predetermined angle, medicine 11c can be securely sucked into syringe 13. The structure shown in FIGS. 11A and 11B makes it possible not only to place ampule 11b upright as shown in FIGS. 4A and 4B, but also to place syringe 13 and ampule 11b at a predetermined angle as shown in FIG. 4C.

As described hereinbefore, in medicine mixing device 10 of the present first embodiment, the mechanism for inclining medicine container 11 at a predetermined angle (the mechanism for changing its posture) periodically inclines medicine container 11 laterally with respect to the vertical direction. This allows a powdery component of a medicine in medicine container 11 to be dissolved in a liquid component of the medicine. The operation of dissolving the powdery material can be performed in the mixture step, that is, in Step S9 shown in FIGS. 5 and 6.

The mechanism for inclining medicine container 11 at a predetermined angle can also be used to mix a plurality of liquid components of a medicine in medicine container 11, allowing medicines to be prepared effectively when they are given to patients.

By using the Medicine mixing device 10 and the method for mixing medicines according to the present first embodiment including the components shown in FIGS. 7 to 14, medicines 11c in medicine containers 11 with different handling characteristics can be mixed quickly and without, waste.

Second Embodiment

Figure 15A:
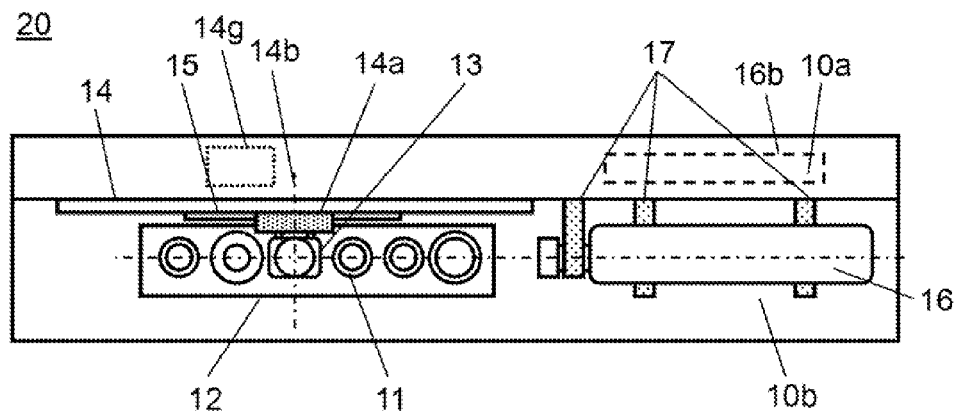
FIG. 15A is a schematic plan view of a medicine mixing device according to a second embodiment of the invention.
Figure 15B:
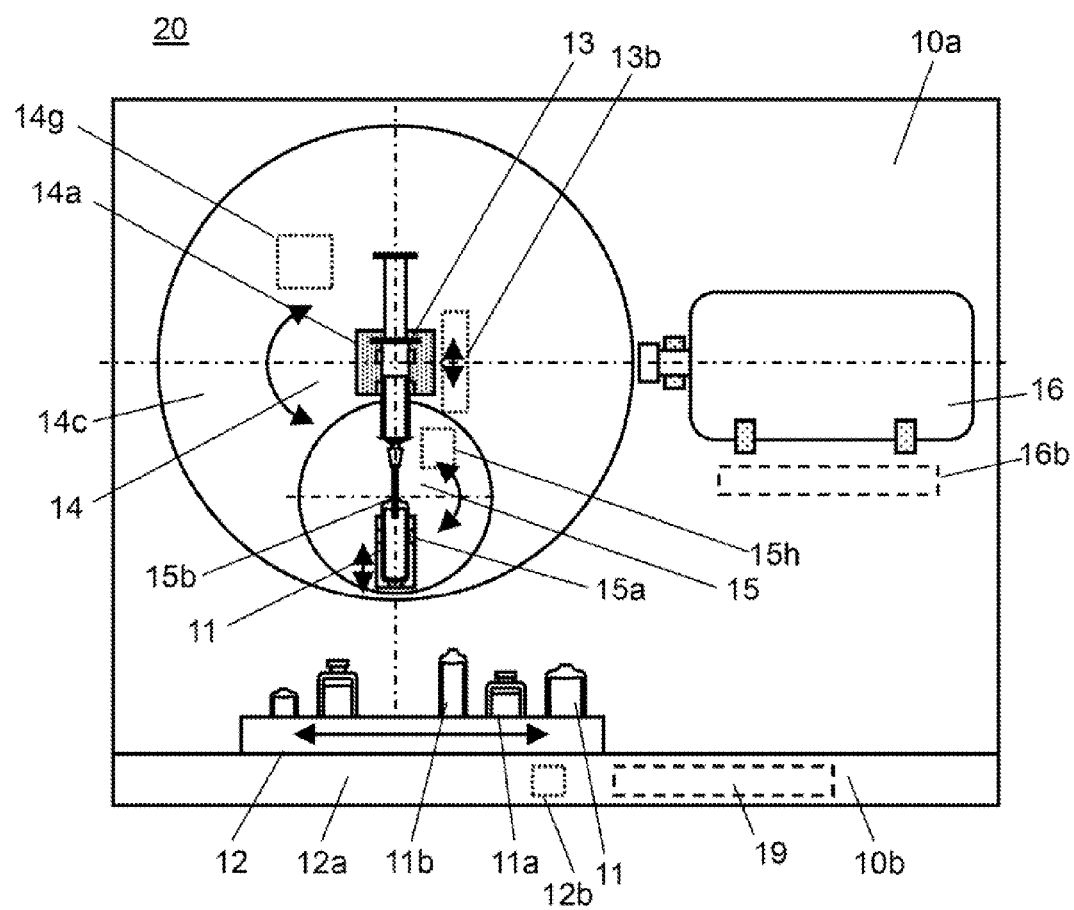
FIG. 15B is a schematic plan view of the medicine mixing device according to the second embodiment of the invention.
Figure 16:
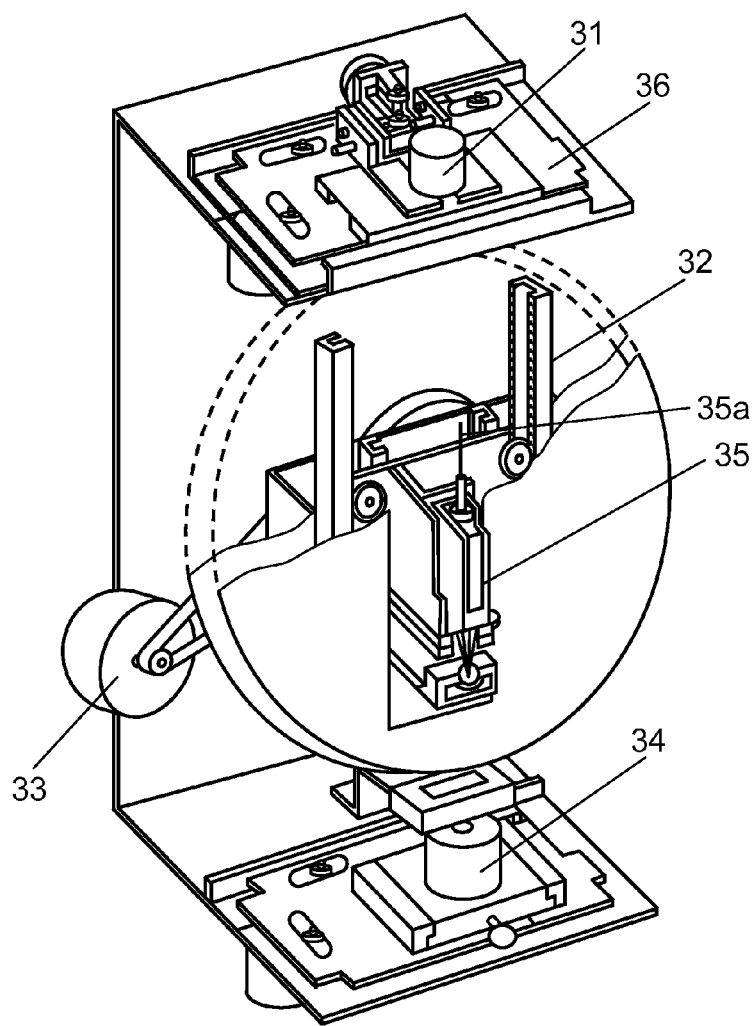
FIG. 16 is a configuration of the radioactive medicine dispensing device of Patent Literature 1.

FIGS. 15A and 15B are a plan view and a schematic front view, respectively, of medicine mixing device 20 according to the second embodiment of the invention. Medicine mixing device 20 includes the same components as medicine mixing device 10 of the first embodiment except that pedestal 12 is a rectilinear rack.

The device with this structure can, by itself, handle medicines 11c and medicine containers 11 such as vial 11a and ampule 11b with different handling characteristics by placing medicine containers 11 in the respective postures that are the most suitable for them to be handled, thereby mixing medicines 11c contained in different medicine containers 11 quickly and without waste.

Medicine mixing device 20 operates in the same manner as medicine mixing device 10 of the first embodiment as follows. In the case of sucking a medicine out of vial 11a as one of medicine containers 11, main and sub rotating bases 14 and 15 are operated in liaison with each other such that vial 11a is placed upside down above syringe 13. As a result, the medicine in vial 11a is sucked into syringe 13.

In the case of sucking medicine 11c out of ampule 11b as one of medicine containers 11, ampule 11b is placed upright under syringe 13. Then, the medicine in ampule 11b is gradually decreased by sucking, according to which main and sub rotating bases 14 and 15 are operated in liaison with each other to move ampule 11b upward. As a result, almost all of medicine 11c can be sucked out of vial 11a or ampule 11b into syringe 13.

The main and sub rotating bases used in the first and second embodiments are spinning discs, but may alternatively be spinning plates or sheets.

The ampules used in the first and second embodiments are made of glass or plastic, but may alternatively be made of other similar materials.

According to the device and method for mixing medicines of the invention, medicines and medicine containers with different handling characteristics can be handled by a device by placing the medicine containers in the respective postures that are the most suitable for them to be handled, allowing a plurality of medicines to be mixed quickly and without waste.

Thus, the invention provides a compact medicine mixing device allowing for safe and efficient, mixing of a plurality of medicines which are contained in different medicine containers with different shapes and materials and which are to be sucked out differently, and an appropriate method for mixing medicines. This greatly reduces the work burden of nurses and pharmacists in hospitals and other facilities.

The invention claimed is:

1. A medicine mixing device comprising:
    a pedestal on which medicine containers are to be placed;
    a main rotating base including a holding portion and a main rotating shaft, and being rotatable around the main rotating shaft, the holding portion being configured to hold a syringe that sucks a medicine at a center thereof on a vertical plane thereof, and the main rotating shaft being orthogonal to the vertical plane;
    a sub rotating base placed on the main rotating base and being rotatable relatively with respect to the main rotating base, the sub rotating base including a fixing unit and a sub rotating shaft parallel to the main rotating shaft, the fixing unit being configured to fix thereto one medicine container selected from the medicine containers on the pedestal; and
    a control unit configured to control a medicine to be sucked out of the fixed medicine container into the syringe.

2. The medicine mixing device of claim 1, wherein
    the medicine containers include a first medicine container and a second medicine container.

3. The medicine mixing device of claim 2, wherein
    the first medicine container is a vial, and the second medicine container is an ampule.

4. The medicine mixing device of claim 1, further comprising:
    an infusion holder configured to hold an infusion bag, the infusion holder including a transfer mechanism that moves the infusion bag with respect to the syringe.

5. The medicine mixing device of claim 1, wherein
    the fixing unit of the sub rotating base includes a retention mechanism that holds the medicine container such that a center of the medicine container coincides with a needle of the syringe.

6. The medicine mixing device of claim 1, wherein
    the holding portion of the main rotating base includes a transfer mechanism movable in an axial direction.

7. The medicine mixing device of claim 1, wherein
    the fixing unit of the sub rotating base includes a transfer mechanism movable in an axial direction.

8. The medicine mixing device of claim 1, wherein
    the pedestal is one of a rectilinear rack and a turntable.

9. The medicine mixing device of claim 8, wherein
    the turntable includes a revolver having a motor at a bottom thereof, the turntable being driven by the revolver.

10. The medicine mixing device of claim 8, wherein
    the one of the rectilinear rack and the turntable is detachable and portable.

* * * * *